United States Patent [19]

Seylar

[11] 4,114,606
[45] Sep. 19, 1978

[54] MONITORING APPARATUS FOR RESONANT CIRCUIT INTRACRANIAL PRESSURE IMPLANTS

[75] Inventor: George R. Seylar, Clarksville, Md.

[73] Assignee: The Johns Hopkins University, Baltimore, Md.

[21] Appl. No.: 741,231

[22] Filed: Nov. 12, 1976

[51] Int. Cl.² .............................................. A61B 5/02
[52] U.S. Cl. ............................. 128/2.05 E; 128/2 P; 73/72.8; 324/57 Q
[58] Field of Search ............... 128/2 P, 2.0 SE, 2.1 A, 128/1.5, 419 R; 73/410, 67.4, 4, 304 C, 718, 724, 728; 324/57 SS, 57 Q, 58.5 B, 61 QS, 61 QL, 58.5 C, 58.5 D

[56] References Cited

U.S. PATENT DOCUMENTS

| | | | |
|---|---|---|---|
| 3,218,638 | 11/1965 | Honig | 343/6.5 |
| 3,426,271 | 2/1969 | Alais | 324/61 QL |
| 3,469,204 | 9/1969 | Magyar et al. | 331/65 |
| 3,504,664 | 4/1970 | Haddad | 128/2.1 R |
| 3,757,770 | 9/1973 | Brayshaw et al. | 128/2 R |
| 3,893,111 | 7/1975 | Cotter | 343/6.5 R |
| 3,906,340 | 9/1975 | Wingfield et al. | 324/57 Q |
| 3,943,915 | 3/1976 | Severson | 128/2 P |
| 3,958,558 | 5/1976 | Dunphy et al. | 128/2 P |
| 4,014,319 | 3/1977 | Faure | 128/2 R |
| 4,026,276 | 5/1977 | Chubbuck | 128/2 P |

OTHER PUBLICATIONS

Sinfield, L. F. "Simple Inductance, Capacitance and Resonance Meter," Wireless World, Feb. 1955, pp. 95–96.
Collins, C. C. "Miniature Passive Pressure Transducer for Implanting in the Eye," IEEE Trans. on Biomed. Engr., vol. BME-14, No. 2, 4/67, pp. 74–83.
McAbel, W. E. "Probe Measurements," pp. 78–92, Tektronix, Inc., 1969.

Primary Examiner—William E. Kamm
Assistant Examiner—Francis J. Jaworski
Attorney, Agent, or Firm—Robert E. Archibald

[57] ABSTRACT

The invention relates to interrogation, detection, and monitoring apparatus useful for monitoring changes in the resonant frequency of a passive L-C circuit implanted in the cranium, the resonant frequency of the implanted circuit varying in a predetermined fashion with changes in the intracranial pressure. The present invention is disposed externally of the skull and provides apparatus for imposing electro-magnetic radiation on the implanted circuit, the frequency at which the radiation is absorbed being then detected and converted into an indication of intracranial pressure.

6 Claims, 3 Drawing Figures

MONITORING APPARATUS FOR RESONANT CIRCUIT INTRACRANIAL PRESSURE IMPLANTS

STATEMENT OF GOVERNMENT INTEREST

The invention described herein was made in the course of work under a grant or award from the Department of Health, Education, and Welfare.

BACKGROUND OF THE INVENTION

A. Field of the Invention

The invention finds utility for monitoring intracranial pressure in diagnostic and post-operative situations, the present invention comprising "bed-side"-apparatus for monitoring pressure-sensitive circuitry which is implantable in the cranium.

B. Description of the Prior Art

The need for monitoring intracranial pressure has long been recognized for applications involving intracranial hyper-tension. Although such a need is well-identified for hydrocephalic individuals and individuals who have undergone neurosurgery, other critical situations involve individuals subject to brain swelling, edema, obstruction of cerebral spinal fluid pathways, or intracranial space-occupying lesions. Accurate monitoring of the intracranial pressure in certain of these situations allows institution of emergency procedures should pressure rise to dangerous levels.

Common methods for measuring intracranial pressure involve implantation of a pressure transducer having wires which pass through the skull and scalp. Measurement of the pressure of the cerebral spinal fluid, which can be related to the intracranial pressure, has generally involved lumbar puncture or introduction of a catheter into the ventricular spaces. None of these techniques are suitable for prolonged measurement of these pressures. Danger of infection, patient discomfort, and the certain need for a second operation to remove the measuring device are negative aspects of all of these prior art techniques. Certain of these techniques actually cause leakage and blockage of the hydraulic system within the cranium and directly affect pressure measurements.

A number of intracranial pressure measurement systems have been postulated and even tested in recent years. Virtually all of these systems involved placement of a transducer within the cranium with wires passing through the scalp to a recordation sub-system. Use of these systems posed a constant risk of infection and required constant adjustments to compensate for changes in the position of the patient. Such systems were necessarily short-term in use. Attempts were made by Atkinson et al and Olson et al in 1967 and 1968 respectively to implant a variable capacitor mounted on two sides of an air-filled tambour, the resonant frequency of the variable tuned circuit then being read by imposing a radio wave thereon through the intact scalp. The devices thus proposed were subject to extreme fragility and needed to be constantly recalibrated for temperature and atmospheric pressure changes. Further, error was prevalent in the use of these devices due to drift in the zero reading, i.e., "baseline dirft."

SUMMARY OF THE INVENTION

The invention provides a system for monitoring from a location external of the skull the resonant frequency of a circuit contained within an implanted transducer either within or proximous to the cranial cavity, the circuit having a natural frequency influenced by ambient pressure. The implanted circuit can be of the kind described in U.S. Pat. application Ser. No. 673,970, filed Apr. 5, 1976 by John G. Chubbuck, which has now matured into U.S. Pat. No. 4,026,276, issued May 31, 1977, and which has a common assignee with the present application. Such implanted circuits are passive transducers having inductance and capacitance capabilities and which operate to compare the environmental pressure of the implant, i.e., the intracranial pressure, to a reference pressure. Changes in the resonant frequency of such circuits can be related to intracranial pressure, such changes being detected by observation of the frequency at which energy is absorbed from an imposed electromagnetic field located externally of the cranium.

The invention particularly comprises a system for either continuously or intermittently monitoring the subcutaneous implanted circuit by imposing electromagnetic radiation on the circuit, detecting the frequency at which maximum absorption of the radiation occurs, and converting the detected frequency into an indication of intracranial pressure. The passive implantable circuits which are particularly useful with the present invention can be either permanently or temporarily placed in a trephine or "burr" hole in the skull, the scalp being fully closed over the implant. The implanted circuit is therefore monitored by the present invention without the need for percutaneous extracranial connections to the present apparatus.

As noted in part above, measurement of intracranial pressure gradients are necessary to anticipate and thereby effectively treat secondary complications of cerebral insults, such as transtentorial herniations, obstructive hydrocephalus, and rapidly expanding hematomas. The present invention allows ready determination of specific treatment modalities to reverse these complications as well as providing useful information in the treatment of cerebral edema of idiopathic hydrocephalus in children. Since individuals in whom intracranial pressure monitoring is most desirable are those in whom neurosurgical intervention is necessary or anticipated, the unavoidable requirement for a small burr hole through the skull is acceptable. However, the present invention allows operation without the need for electrical circuits or manometric conduits which extend through the scalp, both of which offer a portal of entry for infection and compromise patient mobility.

Accordingly, it is a primary object of the invention to provide a system for monitoring intracranial pressure without the need for percutaneous extracranial electrical connections or manometric conduits.

It is a further object of the invention to provide monitoring apparatus for detecting through the scalp the resonant frequency of an implantable pressure transducer, the frequency being an indication of intracranial pressure.

It is another object of the invention to provide extracranial apparatus for interrogating an implantable pressure transducer by imposing electromagnetic radiation on the transducer through the scalp, the frequency at which the transducer absorbs the radiation being detected and converted to an indication of intracranial pressure.

It is yet another object of the invention to provide "bed-side" monitoring apparatus which continuously or intermittently indicates the intracranial pressure of an individual having a passive L-C circuit type transducer implanted subcutaneously in the cranium.

Further objects and advantages of the invention will become more readily apparent in light of the following detailed description of the preferred embodiments of the invention.

DESCRIPTION OF THE PREFERRED EMBODIMENTS

Figure 1:
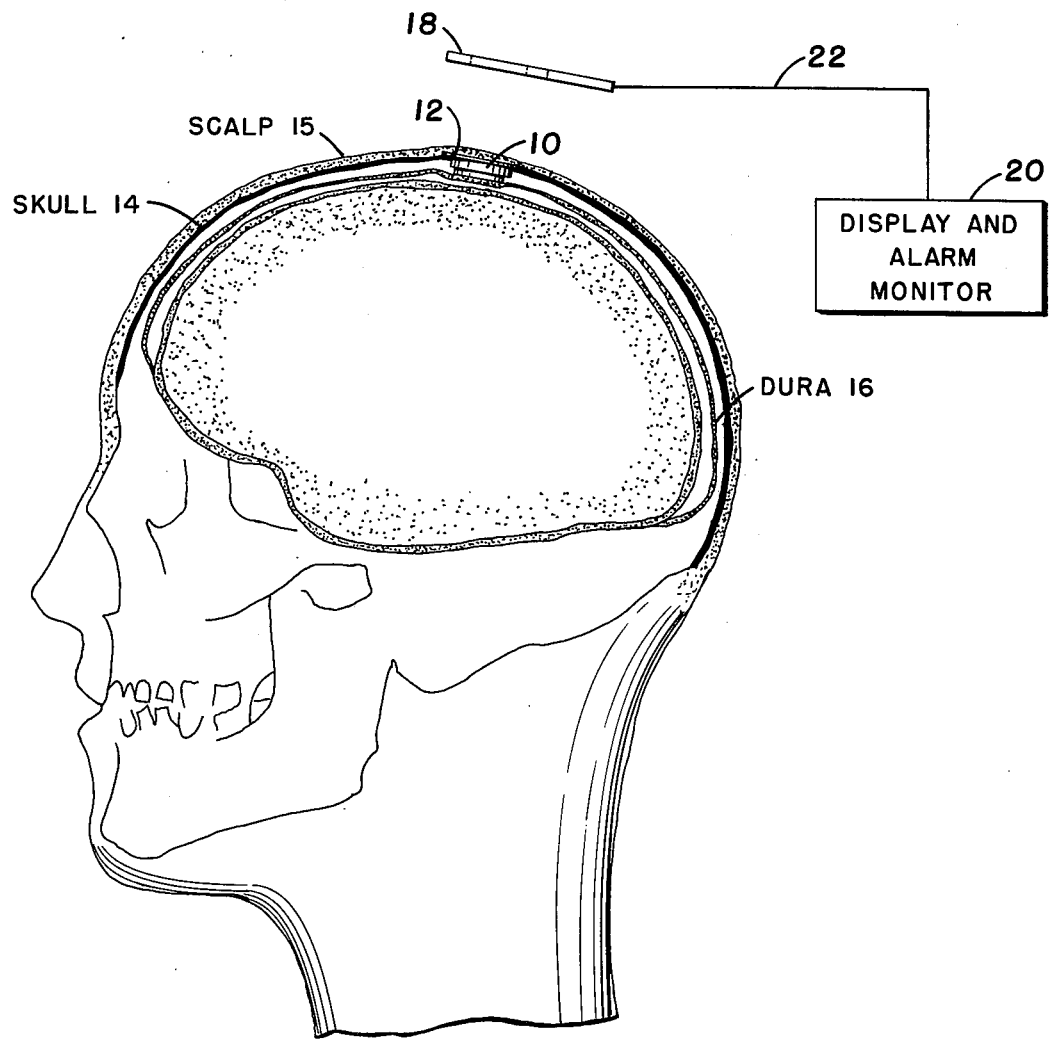
FIG. 1 is a schematic illustrating the environment of the invention.
Figure 2:
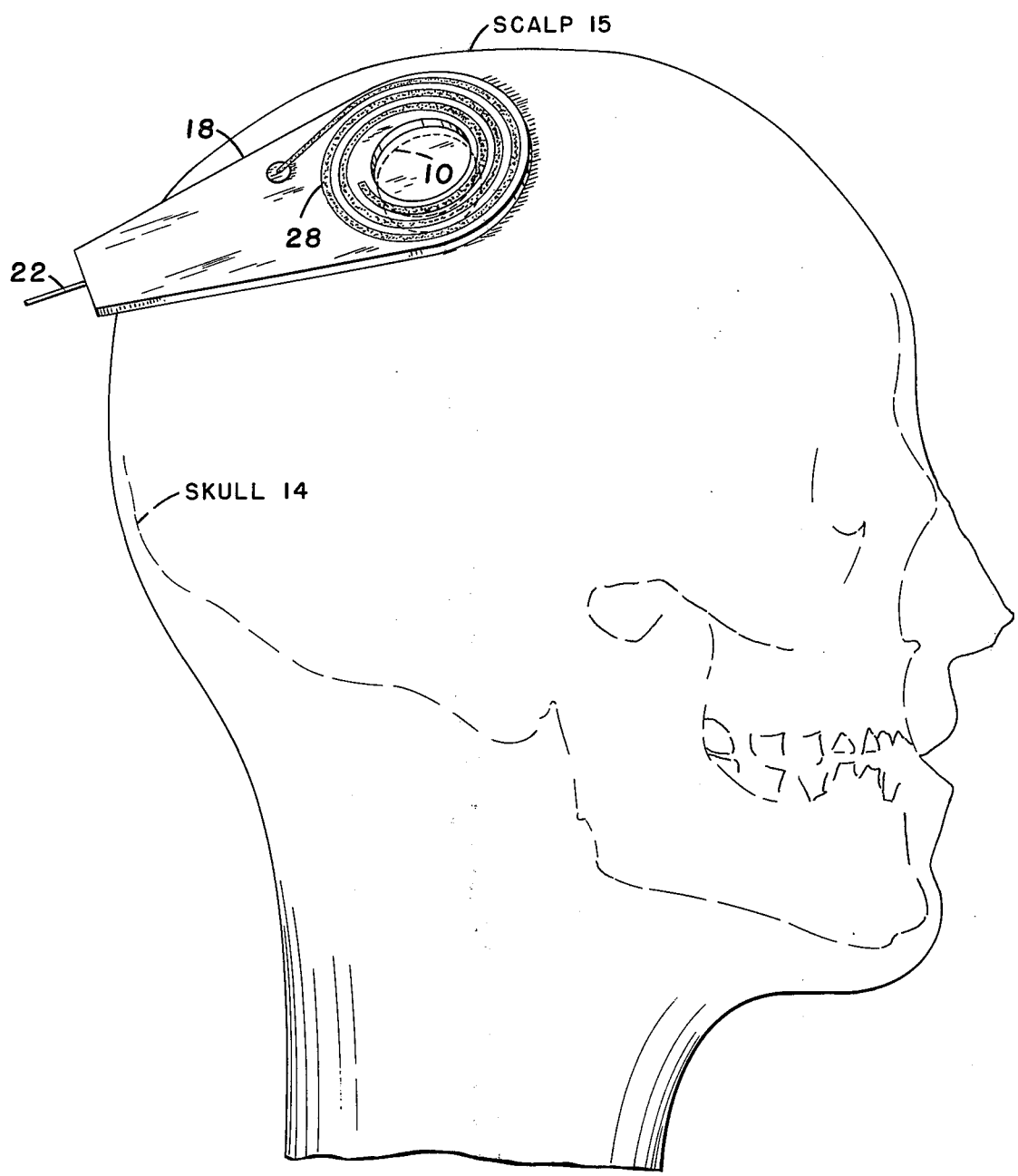
FIG. 2 is an idealized perspective illustrating the placement of the detector element of the invention over the implanted pressure transducer; and, FIG. 3 is a block diagram illustrating the electrical components of the implanted transducer, the external detector, and the external monitoring apparatus used to detect and monitor the resonant frequency of the transducer.

Referring to FIGS. 1 and 2, an implantable pressure transducer is seen at 10 to be positioned within a burr hole 12 in the skull 14 of an individual who has need for monitoring of the intracranial pressure. The lower face of the transducer 10 is seen to be preferably positioned against the dura 16, a membrane which lies beneath the skull 14 and above the subarachnoid space, i.e., the space between the skull 14 and the brain. Pressure sensed by the transducer 10 is measured by an external detector 18 which is positioned externally of the scalp 15 over the implanted transducer 10, the detector 18 being electrically connected to a display and alarm monitor 20. Through use of the present detector 18 and monitor 20 in a manner to be described hereinafter, a continuous display of intracranial pressure can be made. Additionally, a visual or audio alarm can be integrated into the monitor 20 to provide a signal when intracranial pressures reach dangerously high (or low) levels.

Prior to description of the detector 18 and monitor 20, a brief description of the nature of the transducer 10 will be given. The transducer 10 is preferably of the kind described in U.S. patent application Ser. No. 673,970, filed Apr. 5, 1976, by John G. Chubbuck, which has matured into U.S. Pat. No. 4,026,276, issued May 31, 1977. The transducer 10 contains a passive radio-frequency circuit which has a natural frequency which is influenced by the pressure of the transducer's environment, i.e., as seen in FIGS. 1 and 2, the intracranial pressure. The transducer 10 can be configured to compare the environmental pressure with the pressure of a fixed mass of gas entrapped within the transducer. Alternatively, the transducer 10 can be configured to provide a measure of the difference in pressure between the environmental pressure, i.e., the intracranial pressure, and the pressure immediately beneath the scalp, which pressure is representative of barometric pressure. A transducer of the type employed with the present invention must be formed such that the resonant circuit within the transducer is coupled to the radio-frequency electromagnetic field imposed on the transducer by the external monitoring apparatus of the invention.

As has previously been briefly described relative to FIG. 2, the external detector 18 is brought into spaced relationship to the implanted transducer 10 on closure of the scalp 15. The detector 18 is usually taped or manually positioned on the surgical dressing which overlies the site of the implanted transducer 10. As will be soon described in detail, the detector 18 interrogates the implanted transducer 10 by directing electromagnetic energy into the transducer, the frequency at which the transducer absorbs the incident electromagnetic energy being indicative of the intracranial pressure sensed by the transducer. The detector 18 is connected to the monitor 20 as aforesaid, the monitor 20 operating continuously to provide a display of the intracranial pressure. The monitor 20 can be configured to provide a permanent recording of the pressure.

A visual or auditory alarm made a part of the monitor 20 can be caused to operate if the sensed pressure reaches certain predetermined levels. The monitor 20 can also be designed so that it will not respond to the momentary increases in pressure such as are typically brought about by coughing or straining. Since the transducer 10 in certain forms thereof essentially acts as a small barometer and is thereby responsive to absolute pressure, correction for barometric pressure can be included in the monitor 20 itself. Alternatively corrections can manually be made in response to barometric pressure changes.

As indicated previously, the detector 18 is placed over that location on the scalp which surmounts the implanted transducer 10. The resonant frequency of the transducer circuit is then determined by subjecting the circuit to a frequency swept RF signal radiated from the detector 18, the frequency at which the electromagnetic energy is most efficiently coupled into the transducer circuit, wherein said energy is dissipated by resistive losses, then being detected by the detector 18.

Figure 3:
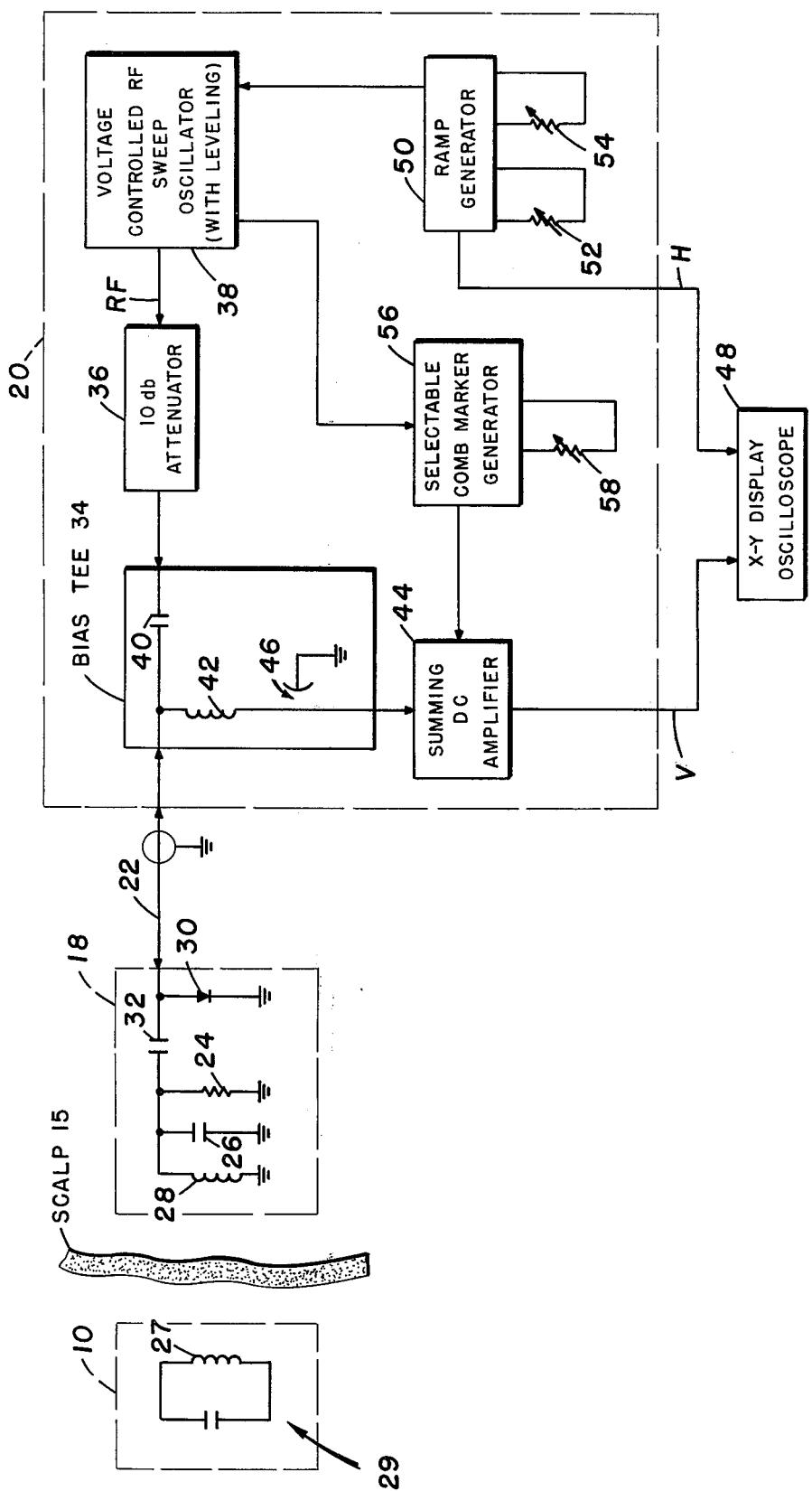

The apparatus of the invention which remotely imposes and electromagnetic field on the transducer 10 and remotely indicates the frequency at which energy is absorbed by the transducer is shown in FIG. 3. The detector 18 is seen to be electrically joined to the monitor 10 by means of a single coaxial transmission line 22 which conveys RF signals from the monitor 20 to the detector 18 and simultaneously returns the signal detected by detector 18, which detected signal appears as a DC voltage, to the monitor 20. Although separate coaxial cables could be used to separately convey the RF input and the DC output, the presence of two separate cables attached to the detector 18 results in inflexibility of the combination, the detector 18 thereby being less handy to use for routine monitoring.

The RF input to the detector 18 typically has a characteristic impedance of 50 ohms, the signal being driven by a swept frequency signal source in the monitor 20 which has an output impedance of 50 ohms. A 50 ohm resistor 24 is present in the circuit of the detector 18, the resistor 24 minimizing the SWR over the operating frequency band so that reflections do not cause extraneous frequency dependent peaks and nulls. A parallel resonant LC circuit comprised of capacitor 26 and inductor 28 is placed across the transmission line 22. The bandwidth of this resonant circuit is intentionally made large by using a large L to C ratio along with the heavy resistive loading caused by the resistor 24 in parallel with the 50 ohm RF source resistance, inductor losses being comparatively negligible. The inductor 28 is physically constructed and positioned in the detector 18, to maximize inductive coupling with an inductance coil 27 of a resonant circuit 29 in the implanted transducer 10. The inductor 28 itself essentially takes the form of a coil. A diode 30 detects the RF signal appearing across the inductor 28 and produces a DC voltage output which is proportional to the existing RF voltage. The diode 30 is positioned in the detector circuit so that this resulting DC voltage appears on the RF input transmission line. A low RF impedance coupling capacitor 32 passes the RF signal to the resistive termination and to the broadband resonant LC network. The capacitor 32 also blocks the DC voltage signal from being short circuited to ground through the inductor 28.

In normal operation the RF signal source in the monitor 20 (to be described in detail hereinafter) is swept linearly from 50 $MH_z$ to 100 $MH_z$ at a 60 $H_z$ rate and provides a constant output power level of about 1 milliwatt (OdBm). The output power level is preferably maintained at a constant level over the sweep range to within ± 0.25 db. In the absence of inductive coupling, the RF voltage at the detector 18 remains constant throughout the sweep range. The resulting DC output voltage is likewise constant.

When the resonant circuit of the implanted transducer 10 is coupled to the LC circuit of the detector 18, maximum energy is coupled from the detector 18 to the transducer 10 only at the resonant frequency of the transducer. When this energy transfer occurs, an accompanying reduction in the RF voltage appears across the inductor 28. This reduction can be envisioned as either a power transfer which loads down the source of the voltage or equivalently, as an impedance transformer which reflects a low value resistance across the inductor 28. The magnitude of the RF voltage drop is dependent primarily on the amount of inductive coupling which is maximized when the two inductors, i.e., the coil 27 and the inductor 28, are positioned coaxially in the closest possible proximity. The maximum loading effect occurs only at the resonant frequency of the transducer 10; consequently, as the applied RF signal is swept across the operating band, the circuit of the detector 18 will respond to a dip in RF voltage across the inductor 28 as the swept signal passes through the resonance of the transducer 10. The bandwidth of this dip is determined jointly by the Q of the resonant circuit 29 of the transducer 10 and by the amount of inductive coupling. Low Q and tight coupling increase bandwidth and impair resolution of the resonant frequency. By correlating the occurrence of the voltage dip with the frequency of the source of sweep generation, the frequency of resonance is determined, the intracranial pressure being related thereto.

In order to recover the DC voltage signal from the transmission line 22 and to prevent said signal from being loaded by the RF signal source, a bias tee 34 is provided in the transmission line 22, the bias tee 34 being integrated into the monitor 20. The bias tee 34 receives the RF voltage signal through a 10 db attenuator 36 from a voltage controlled RF sweep oscillator 38. The bias tee 34 essentially consists of a low RF impedance coupling capacitor 40 which passes the RF voltage signal from the sweep generator 38 and blocks the DC voltage signal returning from the detector 18. The DC voltage signal is shunted through a radio frequency choke 42 in the bias tee 34, the choke 42 appearing as a negligible high impedance to the RF signals while passing the DC signal to a DC amplifier 44. A low RF voltage feed through capacitor 46 positioned between the choke 42 and the amplifier 44 acts to prevent RF signals from being passed on to the amplifier 44. The amplifier 44 can typically provide a 10,000 ohm DC load to the detector 18 and produces an inverting DC gain of 20. The DC output of the detector 18 is typically on the order of −50 mV, thereby producing a +1.0 volt output from the amplifier 44. Typical component values in the bias tee 34 are 2,000 pf for the capacitor 40, 2.2 $\mu$h for the RF choke 42, and 1,000 pf for the capacitor 46. In the detector 18, typical component values are 1,000 pf for the capacitor 32, 51 ohms for the resistor 24 and 10 pf for the capacitor 26. The diode 30 can be a Schottky barrier type, a suitable inexpensive commercial version of which is the HP 5082-2800.

The inductor 28 takes the form of a flat spiral inductance coil, which coil can be formed on a flat PC-type board. In such a typical construction, the inductor 28 would exhibit an inductance of 0.305 microhenrys and would have a self resonant frequency of about 270 $MH_z$, thereby indicating a stray capacitance of about 1.1 picofarad. When using an additional 10 pf capacitor, the circuit of the detector 18 resonates at about 87 $MH_z$, such resonance providing an essentially constant, slightly rounded response from 50 $MH_z$ to 100 $MH_z$ with only a slight midband peak.

The monitor 20 is configured to drive a commercial X-Y display oscilloscope 48, such as the Telonic Model 121 or the Wavetek Model 1901A. The monitor 20 itself can consist primarily of a commercially available RF sweep generator such as the Wavetek Model 1050A sweep generator, this commercial unit being modified in several ways. Primarily, this commercial sweep generator is modified by adding the bias tee 34 for extraction of the DC voltage signal from the detector 18 and by adding the DC amplifier 44 for increasing the DC signal. Frequency marker signals to be described hereinafter are also added to assist in signal processing. Other functions added to this commercial sweep generator include: (1) restriction of the frequency range of the center frequency control to a desired band; (2) replacement of the RF output step attenuator with the 10 db attenuator 36 to set the output level at OdBm; (3) replacement of the RF output vernier control with a fixed setting; (4) removal of the demodulator input connection; (5) repositioning, calibration, and limiting the range of the sweep width control; (6) replacement of the marker width control with a fixed value; (7) rewiring of the AC power switch to break both sides of the line; and, (8) fabrication of a control panel with controls labeled and positioned to facilitate use of the monitor 20.

The monitor 20 is configured as specifically seen in FIG. 3, the sweep oscillator 38 providing an RF output restricted to the frequency range of approximately 50 $MH_z$ to 100 $MH_z$. An output level of about + 10 dBm is controlled and maintained at a constant level across the sweep range of the oscillator 38 by an internal active leveling circuit (not shown). A frequency control voltage which is fed into the oscillator 38 is obtained from ramp generator 50. The ramp from the generator 50 being shaped to compensate for nonlinearities in the oscillator 38 so that a linear frequency sweep results. Sweep rate is fed at the AC line frequency (60$H_z$). Center frequency of the RF sweep is operator adjustable by a center frequency variable resistor 52 to any frequency in the range between 50 $MH_z$ to 100 $MH_z$. The operator would typically set the center frequency to nearly coincide with the resonant frequency dip displayed on the display oscilloscope 48. The sweep width (or frequency span) is also operator adjustable by a sweep width variable resistor 54 to a nominal range of 1 $MH_z$ to 50 $MH_z$. The operator can adjust the sweep width to obtain the desired horizontal display "magnification" to facilitate resolution of the resonant dip frequency. The resulting sweep voltage is ramped symmetrically both up and down. During the down or retrace sweep, the output amplifiers (not shown) of the oscillator 38 are caused to be inoperative in order to remove the RF output. A zero output reference is thus produced during this interval and appears as a baseline on the oscilloscope 48. The ramp generator 50 also provides a linear ramp (triangular) voltage H which is fed to the oscilloscope 48 to be used as the horizontal drive signal.

The leveled RF output from the sweep oscillator 38 is attenuated by the attenuator 36 to about 0 dBm. At this drive level, the transfer characteristic of the detector 18, i.e., DC out vs. RF power in, begins to become less exponential, i.e., more linear. Increasing the drive level would also increase the amplitude of the resonance dip of the detector 18. However, the average DC output would correspondingly increase in a significantly greater fashion, thereby resulting in the magnitude of the dip being proportionately smaller in relation to the DC level away from resonance. The summing DC amplifier 44 combines the DC output from the bias tee 34 with frequency marker output signals generated by a selectable comb marker generator 56. Demodulated signals from the detector 18 are inverted and amplified by 20 while the marker signals are inverted and amplified by a factor of unity. The resulting signal is fed from the amplifier to the oscilloscope 48 as vertical input V thereto. The marker generator 56 consists of three separate comb frequency generations (not shown), any one or combination of which can be selected by an operator through use of a marker size variable resistor 58. The comb frequency generators are used to determine the frequency at which the resonant dip appears on the display oscilloscope 48. The comb generators produce crystal controlled marker signals having 1 $Mh_z$, 10 $MH_z$, or 50 $MH_z$ spacing. These marker signals are compared with a sample of the swept RF signal through connection to the oscillator 38. When a audio beat frequency is produced by the two signals, the marker generator 56 produces the clipped output marker signal which is sent to the summing DC amplifier 44.

In order to protect the patient from electrical shock hazards, the monitor is isolated from AC power lines by the use of isolation transformers (not shown) in the power supplies. The detector 18 is also insulated. Automatic correction for barometric pressure and patient temperature can also be provided in the monitor 20 in order to produce a direct digital read-out of actual pressure without the need for manual conversion. Such correction would be implemented by a microprocessor which would read in data from a barometric pressure transducer, such as a National Semiconductor LX3701A; decode a manually fed reading of the patient's temperature; perform the frequency counter function to determine the frequency of the variable marker when aligned with the resonant dip (or generate the marker signal with synthesizer techniques); and execute a stored program using this data with pre-determined parameters of the implanted transducer 10 to obtain a digital readout of intracranial pressure.

The physical structure of the detector 18 can vary considerably. As shown in FIGS. 1 and 2, the detector 18 is seen to have a central aperture which is useful for positioning the transducer 10 within the cranium while monitoring the transducer 10 as described by Chubbuck in the aforementioned patent application. The detector 18 can essentially take the form of a printed circuit board having the circuit elements described formed thereon, the shape, thickness and physical conformation of the board being variable as desired.

As should be apparent from the foregoing, the invention can be practiced other than as specifically described hereinabove without departing from the scope and intent of the invention. It is therefore apparent that the invention is to be limited only by the definition provided by the appended claims.

What is claimed is:

1. Apparatus for monitoring an implanted circuit means whose resonant frequency provides indication of a selected physiological activity, comprising:
    an RF sweep frequency generator means for generating an output RF signal whose frequency varies in a predetermined manner throughout an operating frequency range encompassing the resonant frequency of said implanted circuit means,
    a transmission line having one input end connected to receive the RF signal from said sweep frequency generator means, said transmission line having a predetermined characteristic impedance,
    a resistance means connected across the opposite output end of said transmission line and having a resistance value matching the characteristic impedance of said transmission line to minimize the standing wave ration of said transmission line,
    a parallel resonant inductor-capacitor circuit connected across the output end of said transmission line in parallel with said resistance means and adapted to be brought into coupling relationship to said implanted circuit means,
    said parallel connected resistance means and resonant circuit producing a constant broadband response throughout the operating range of said RF sweep frequency generator and a constant value RF voltage across said parallel resonant circuit when not coupled to said implanted circuit means,
    a maximum energy transfer occurring between said parallel resonant circuit and said implanted circuit means, when coupled, when the output signal generated by said RF sweep frequency generator corresponds to the resonant frequency of said implanted circuit means, said maximum energy transfer resulting in a minimum value RF voltage being produced across said parallel resonant circuit denoting the resonant frequency of said implanted circuit means,
    detector means for converting the RF voltage appearing across said parallel resonant circuit to a corresponding DC voltage, and
    indicator means responsive to the value of said DC voltage.

2. The monitoring apparatus specified in claim 1 further including a DC blocking capacitor connected between said detector means and the inductor of said parallel resonant circuit.

3. The monitoring apparatus specified in claim 1 wherein said indicator means is connected to the input end of said transmission line, whereby a single transmission line is utilized for connecting the RF signal from said sweep frequency generator to the parallel resonant coupling circuit and for connecting the DC voltage from said detector means to said indicator means, and further including,
    an RF choke connected between said RF signal generator and said indicator means, and
    a DC blocking capacitor connected between said transmission line and said RF sweep frequency generator.

4. The monitoring apparatus specified in claim 1 wherein said detector means comprises a diode connected in parallel across said parallel resonant circuit.

5. The monitoring apparatus specified in claim 1 further including means connected between said RF sweep frequency generator and said transmission line to minimize changes in the frequency of the RF signal generated by said sweep frequency generator due to coupling of the parallel resonant circuit to said implanted circuit means.

6. The monitoring apparatus specified in claim 1 wherein said indicator means comprises,
a display device,
means connected to said RF sweep frequency generator and said display device for synchronizing the display of said display device to the manner in which said RF signal is generated by said sweep frequency generator means,
means connected to said display device for applying frequency markers to calibrate the display device, and
DC voltage amplifier means connecting said DC voltage to said display means, said display means providing a frequency calibrated display indicative of the resonant frequency of said implanted circuit means.

* * * * *